United States Patent [19]

Laipply

[11] 4,427,115
[45] Jan. 24, 1984

[54] ONE PIECE ALCOHOL PREPARATION DEVICE

[76] Inventor: Thomas C. Laipply, 13530 Fox Den E., Russell, Ohio 44072

[21] Appl. No.: 312,879

[22] Filed: Oct. 19, 1981

[51] Int. Cl.³ .................. B65D 83/00; B65D 75/00; A61B 17/20
[52] U.S. Cl. .................................. 206/484; 206/438; 206/210
[58] Field of Search ............... 206/484, 438, 530, 441, 206/229, 210, 812; 15/104.93; 426/85, 125

[56] References Cited

U.S. PATENT DOCUMENTS

| | | | |
|---|---|---|---|
| 1,529,659 | 2/1925 | Wilkie | 206/530 |
| 1,810,453 | 6/1931 | Webster et al. | 426/85 |
| 2,760,630 | 8/1956 | Lakso | 206/530 |
| 3,527,400 | 9/1970 | Shepherd et al. | 206/438 |
| 3,903,345 | 9/1975 | Baker et al. | 206/484 |
| 3,986,640 | 10/1976 | Redmond | 222/92 |
| 4,372,098 | 2/1983 | Mason | 53/412 |

FOREIGN PATENT DOCUMENTS 613023 1/1961 Canada ........................ 206/438

OTHER PUBLICATIONS

Mason-Keller Corporation, Roseland, New Jersey 07068, U.S.A. M-K Applicator Package, 4/24/78, U.S. Patent No. 4,372,098.

Primary Examiner—William T. Dixson, Jr.
Assistant Examiner—Brenda J. Ehrhardt
Attorney, Agent, or Firm—Maky, Renner, Otto & Boisselle

[57] ABSTRACT

A one piece fluid applying device is formed of flexible material that is folded to form a chamber to contain a fluid. The flexible material is impermeable and unaffected by the fluid. A seal is formed about the chamber to maintain the fluid tight integrity thereof. Surface portions of the flexible material which form walls of the chamber also form surfaces for applying the fluid to another surface, for example, to the skin of a patient.

17 Claims, 7 Drawing Figures

U.S. Patent    Jan. 24, 1984    4,427,115
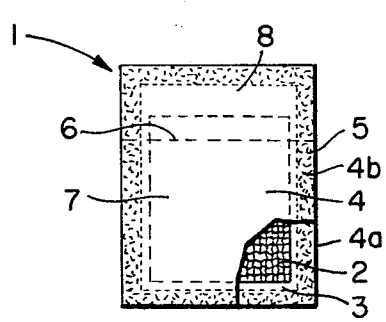
_Fig. 1A_
PRIOR ART
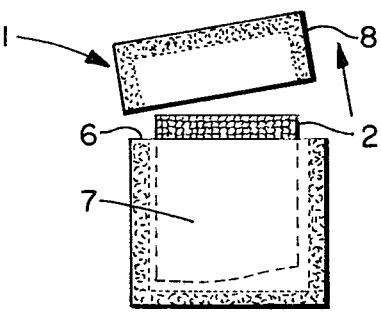
_Fig. 1B_
PRIOR ART
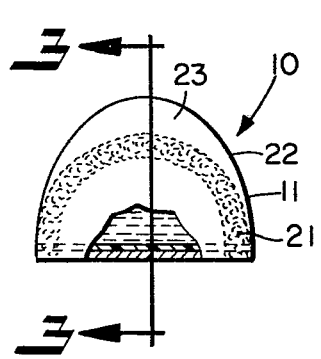
_Fig. 2_
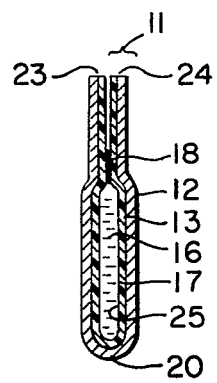
_Fig. 3_
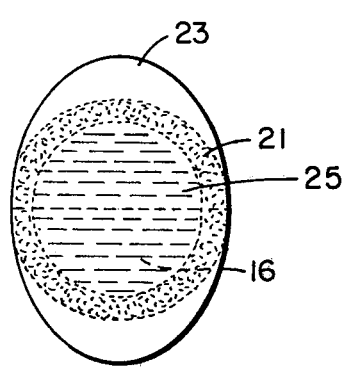
_Fig. 4_
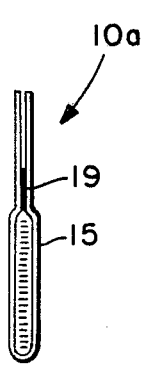
_Fig. 5_
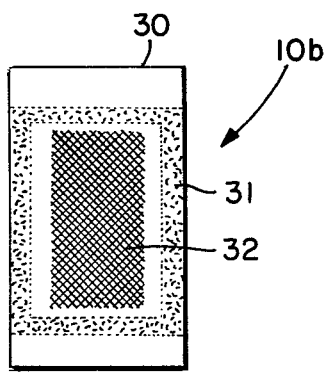
_Fig. 6_

ONE PIECE ALCOHOL PREPARATION DEVICE

TECHNICAL FIELD

The present invention relates generally, as indicated, to fluid applying devices and, more particularly, to such devices in which a fluid is contained in and applied by a single piece of fluid impermeable material.

The invention will be described in detail below as relating to an alcohol preparation device, which is a device that contains alcohol or like fluid intended for sterilizing, cleaning or like purposes. However, it will be understood that the invention encompasses use of fluids other than alcohol or containing alcohol and other materials for sterilizing, cleaning or other purposes.

BACKGROUND OF PRIOR ART

Alcohol preparation devices have been known and used in the medical profession for a number of years. Such devices include alcohol absorbing material, such as gauze or gauze like material which contains alcohol, and a fluid tight protective package that is sealed to define therein a chamber in which the absorbent alcohol containing material is contained. An example of one type of absorbent material is disclosed in U.S. Pat. No. 3,542,634; such material is used in the Webcol alcohol prep device sold by the Kendall Company, Boston, Mass., for example, for the purpose of applying sterilizing isopropal alcohol to the skin of a patient. Another example of such absorbent material and a package for containing the same is disclosed in U.S. Pat. No. 3,057,467; the absorbant material is a folded towelette containing a particular fluid for cleansing and refreshing a user and the package material is, for example, an aluminum foil with a thermoplastic liner. Such package material is impervious to the fluid contained therein, including both the liquid and vapor or gas forms thereof. Such material also is impervious to air and other materials that might otherwise contaminate the fluid and absorbant material contained in the package. The '467 patent discloses polyethylene, polyvinyl resin or cellulose acetate as suitable thermoplastic materials for providing a protective coating on the foil and for providing the impervious vapor-proof barrier desired; such materials also are readily heat sealable to seal closed the package. Other materials of which the package disclosed in the '467 patent may be made are celluloiic materials lined with a thermoplastic film or various synthetic or plastic materials. The device in the '467 patent is manufactured by forming a three part sandwich of two sheets of package material and the folded fluid impregnated towelette therebetween, and the edges of the package material sheets are heat sealed to each other about the entire perimeter of the package.

Several disadvantages inure to the prior fluid applying devices, such as the prior alcohol prep devices, towelette devices, etc. One disadvantage is that the package material must be torn to open the same in order to remove the absorbent material. Upon tearing of the package, the absorbent material may be torn, which may reduce usefulness thereof. Also, when the package is torn it may result in one and possibly two pieces and must be discarded, depending upon whether the tear fully severs one part from the other; and eventually the absorbent material also must be discarded separately. The separate discarding steps may waste time and may result in one or more pieces not reaching a proper waste container, e.g. a piece may drop on the floor and create a safety hazard. A further disadvantage particularly with respect to prior alcohol prep devices is that the user, such as a medical technician, nurse or physician, must physically touch surfaces of the absorbent material; this increases the potential hazard of contamination of the sterile condition of the absorbent material and frequent touching of that material often tends substantially to dry the skin of such user. Moreover, frequent flexing of the heat sealed package may result in loss of the seal integrity.

BRIEF SUMMARY OF THE INVENTION

With the foregoing in mind, the invention has as an objective overcoming of one or more of the above disadvantages of fluid applying devices, and especially those of the type known as alcohol preparation devices.

Accordingly, a primary object is to improve fluid applying devices.

Another object is to enable opening of an alcohol preparation device or the like without having to tear the package thereof.

An additional object is to enable opening of an alcohol preparation device or the like without producing multiple scraps.

A further object is to reduce exposure of a user of an alcohol preparation device or the like to fluid contained therein.

Still an additional object is to improve the sterility of fluid applying material, e.g. of an alcohol preparation device or the like, especially during use thereof, and to improve the sterility of a fluid applying technique.

Still a further object is to improve the integrity of the seal of an alcohol preparation device or the like.

Yet another object is to improve the fluid tight integrity of an alcohol preparation device or the like.

Yet an additional object is to facilitate manufacturing of alcohol preparation devices or the like.

Yet a further object is to minimize the material required for an alcohol preparation device or the like.

Even another object is to minimize the cost of an alcohol preparation device or the like.

Even an additional object is to facilitate opening an alcohol preparation device or the like.

Even a further object is to provide an improved technique for use of an alcohol preparation device or the like.

Moreover, an additional object is to facilitate and to expedite sterilizing procedures.

Moreover, a further object is to avoid separate throw away pieces from a portable fluid applicator.

Yet even another object is to avoid tearing absorbent material of a fluid applying device.

Yet even an additional object is to provide a single piece device for storage and application of a fluid by a single sheet of material.

Yet even a further object is to permit use of a single piece fluid applicator without disrupting physical integrity of the device.

These and other objects and advantages of the invention will become more apparent as the following description proceeds.

In accordance with one aspect of the invention, a one piece fluid applying device consists of flexible material for containing fluid, the flexible material means being folded to form the boundary of a chamber. A seal seals the chamber and a quantity of fluid is located in the chamber.

According to another aspect, a one piece fluid applying device is formed by flexible material having surfaces that form walls of a chamber, a seal for sealing closed the chamber, a fluid contained in the chamber, and wherein the walls of the flexible material that form the chamber also, when the device is open, thus opening the chamber, may be used to apply fluid to, for example, an external surface, such as the skin of a patient.

According to an additional aspect, a method of applying a liquid to an external surface includes opening the seal of a chamber formed by flexible material having wall surfaces that ordinarily bound the chamber and on which liquid from the chamber is coated, and wiping such surfaces to apply the liquid to such external surface.

To the accomplishment of the foregoing and related ends, the invention, then, comprises the features hereinafter fully described in the specification and particularly pointed out in the claims, the following description and the annexed drawings setting forth in detail certain illustrative embodiments of the invention, these being indicative, however, of but several of the various ways in which the principles of the invention may be employed.

BRIEF DESCRIPTION OF THE DRAWINGS

In the annexed drawings

FIGS. 1A and 1B are plan views of a prior art fluid applying device of the alcohol preparation type or alcohol wipe type;

FIG. 2 is a plan view, partly broken away in section, of a one piece fluid applying device in accordance with the present invention;

FIG. 3 is a section view of the device of FIG. 2 looking generally in the direction of the arrows 3—3;

FIG. 4 is a plan view of the device of FIG. 2 with the flexible material thereof being fully open to expose the liquid coating the same for application to an external surface;

FIG. 5 is a section view of a modified one piece fluid applying device in which the flexible material is comprised of a paraffin or wax material; and FIG. 6 is a further modified device in which a surface of the flexible material that forms boundary walls for the fluid chamber is roughened to facilitate holding fluid material thereon.

BRIEF DESCRIPTION OF PRIOR ART FLUID APPLYING DEVICES

Referring briefly to FIGS. 1A and 1B, a prior art alcohol preparation device or alcohol wipe of the type mentioned above with reference to the Webcol device and the '634 and '467 patents is shown at 1. The device 1 includes a pad 2 of absorbent material for containing alcohol, such as, for example, a 70% isopropyl alcohol liquid. The pad 2 is contained in a chamber 3 formed in a package 4. The package 4 typically is formed of a metal foil that is coated or lined with thermoplastic material, for example, as is disclosed in the '467 patent. The lining material faces the chamber 3 so as to provide a fluid impermeable barrier to prevent escape of the alcohol by leakage, evaporation, or the like. The metal foil also provides a fluid impermeable barrier not only for the alcohol but also to prevent contamination of the materials in the chamber 3 from outside the package 4. The foil also provides additional support strength for the device 1. The package 4 is formed of two sheets 4a, 4b of such lined foil material, and the sheets are heat and/or pressure sealed to each other at respectively adjacent overlapping edges thereof around the perimeter of the device 1. The seal is indicated at 5 in FIGS. 1A and 1B.

A dashed line 6 in FIG. 1A is the tear line separating the main body 7 of the package 4 and a tear strip portion 8 thereof. During use of the device 1 a user tears the same approximately along the tear line 6 to separate the tear strip 8 in the manner shown in FIG. 1B exposing the chamber 3 and the pad 2 therein. Usually the tear strip 8 is totally separated from the body 7 and is discarded. After the pad 2 has been removed from the body 7, the latter also is discarded and the pad may be grasped manually by a user to apply alcohol to the surface, for example, the skin of a patient. The pad 2 subsequently may be discarded.

DETAILED DESCRIPTION OF THE INVENTION

As distinguished from the intentionally separable parts of the prior art device 1, the fluid applying device in accordance with the present invention is formed by a single sheet of material for containing liquid in isolation in a chamber and for applying that liquid upon opening the device to use a surface of the sheet to apply the liquid. The device does not have intentionally separable parts and can in fact be stored and used without destroying the attached or structural integrity thereof.

Referring now to FIGS. 2-4, a one piece fluid applying device in accordance with the present invention is generally indicated at 10. The device 10 is formed of a single piece of flexible material 11. The material 11 may be of the types disclosed in the '467 patent or of the type used in the Webcol device; an example of such material includes a metal foil 12 having an inner thermoplastic liner 13. However, in the preferred embodiment and best mode of the present invention, the material 11 is formed of a plastic, paraffin or wax material, such as that sold under the trademark PARAFILM by the American Can Company. Such PARAFILM material is illustrated at 15 in FIG. 5.

The material 11, 15 or any other material of which a one piece fluid applying device in accordance with the invention is formed should be relatively flexible, should be unaffected by the liquid, or other fluid, 16 contained in the chamber 17 formed by the material, and should be capable of being sealed, for example, by the seal represented at 18 in FIG. 3 and 19 in FIG. 5. The flexible material should be adequately strong to resist undesired penetration. The seal should have suitable longevity to avoid leakage or evaporation of liquid therefrom. The liquid 16 may be of the type that cleanses, sterilizes, refreshes, or the like.

The material 11 provides a plurality of functions. Such material has a fold 20 that provides part of the sealing function for the chamber 17 along a continuous linear edge thereof. The seal 18, on the other hand, provides a fluid tight seal for the chamber 17 in the seal zone 21 that extends approximately along or nearly parallel to a perimeter of the device 10 at or near the edge 22 thereof. Most preferably the shape of the material 11 is oval when open, as is seen in FIG. 4, and is of semi-oval configuration when folded in the manner illustrated in FIGS. 2 and 3. On the other hand, preferably the seal zone 21 is approximately a semicircular annulus when the device is folded and would appear generally circular when the device 10 is open in the manner shown in FIG. 4. As a result of such oval/circular or semi-oval/semicircular relationships, portions, tabs, or extensions 23, 24 of the flexible material 11 are relatively accessible and are unsealed so that they may be grasped manually by a user. Such a user may apply force to such portions 23, 24 tending to separate them in order to breach the integrity of the seal 18 opening the folded device to its open form shown in FIG. 4. Upon such opening the liquid 16 becomes accessible.

Accordingly, further functions of the material 11 are to provide the tab portions 23, 24 to facilitate opening of the device 10 and, very importantly, to provide the wall surface area 25 (FIG. 4), which previously provided the boundary walls for the chamber 17, for applying the liquid 16 to another surface, object or the like.

A user may use the device 10 after separating the tab portions 23, 24 to open the device in the manner shown in FIG. 4, by grasping one of the tab areas 23, for example, between the thumb and a finger; and using other fingers of the same hand behind the surface 25 to provide support thereby, may wipe the surface area 25 against an external surface or device intended to have the liquid 16 applied thereto.

An advantage of using the thermoplastic lined material 11 is that the seal 18 may be formed by applying heat to the seal zone 21, whereupon the plastic material of opposed material portions when the device is folded will heat seal to each other. Alternatively and/or additionally mechanical pressure may be applied to the seal zone 21 to form the seal 18. As a further alternative, fluid, semisolid or solid means may be applied at the seal zone 21 to form or to help form the seal 18. An advantage of using the fold 20 as part of the seal for the chamber 17 is that such fold area will provide a rather strong seal integrity thereat, thus reducing portions of any seal that ordinarily might encounter a flaw.

It is desirable that the surface area 25 have a relatively high surface energy so that the liquid 16 will substantially uniformly coat the surface. Accordingly, the liquid should have a satisfactorily low surface tension in order to maintain such coating uniformity or, at the least, complete coating of the surface 25. On the other hand, the liquid should have an adequately high surface tension to facilitate containment thereof in the chamber 17 and sealing of such chamber. Examples of such liquid may be an alcohol or alcohol-containing solution, such as a 70% isopropyl alcohol in solution with water. The alcohol also may be a methyl alcohol or an ethyl alcohol. Examples of alcohol that may be used are as follows: polyoxyethylene sorbitan monolaurate, polyoxyethylene sorbitan monopalmitate, polyoxyethylene sorbitan monostearate, and polyoxyethylene sorbitan mono-oleate. Another example is a material sold under the name Nonidet P-40, which is an octyl phenol ethylene oxide condensate containing an average of 9 moles ethylene oxide per molecule. Moreover, if desired, to assure good coating of the liquid over the surface 25, a wetting agent may be used in solution with the liquid 16. An example of such a wetting agent is sold as Wetting Agent H by J. T. Baker Diagnostics Chemical Co., Bethlehem, Pa.

Briefly referring to FIG. 5, the preferred embodiment and best mode of the present invention is embodied in the device 10a. Such device is substantially the same as that described above with reference to FIGS. 2–4, but as was mentioned earlier, the material 15 of which the device is formed is comprised of a plastic paraffin or wax material. Such material 15 has a good flexibility characteristic and a good integrity characteristic. Moreover, such material is relatively light weight and inexpensive. Additionally, such material 15 is directly responsive to application of heat to form the seal 19. The shape of the device 10a would be preferably the same as the shape illustrated in FIGS. 2–4, namely, an oval shape having a circular seal zone when the device is open; and a semi-oval shape with a semicircular seal zone when the device is folded in the manner illustrated in FIG. 5.

Either of the devices 10, 10a also may be formed in shapes other than oval ones. For example, as is shown in FIG. 6, such devices may be rectangular, or they may be diamond shape when open or any other shape, as may be desired. An advantage to a diamond shape configuration, which is not shown herein, is the availability of the free apexes, i.e., those that do not join a fold, of the triangles that are formed when the device is folded to form a chamber, such as the chamber 17, for use to facilitate manual grasping of the device to open the same, etc., as was described above.

As is seen in FIG. 6, a one piece fluid applying device 10b in accordance with the invention is formed of a rectangular flexible material 30 having a rectangular seal zone 31. The device 10b is illustrated in open position ready for use to apply fluid contained in the area 32 to an external surface. The surface 32, moreover, has been roughened or knurled or otherwise pretreated or prepared so as to increase the quantity of liquid that can be contained by or adhered to the surface. Roughening of the surface 32 not only will increase the quantity of fluid that can be adhered thereto but also may be used to effect some abrasion of a surface to which the liquid is to be applied thereby to assist in effective application of the liquid to such external surface.

Further to assure the effective coating of the external surface with such liquid, it is important that the liquid contained by the surface 25 or 32 of the present invention not undergo covalent bonding with the liquid.

STATEMENT OF INDUSTRIAL APPLICATION

With the foregoing in mind, it will be appreciated that the invention provides a one piece fluid applying device and method for applying fluid of, for example, cleansing, sterilizing, refreshing, or like types to an external surface.

I claim:

1. A combined fluid storage container and applicator device for relatively inviscid fluids such as alcohols and iodine, said device comprising a single integral sheet of fluid impermeable material folded in generally symmetrical halves over on itself along a fold line positioning said halves in flat parallel overlying relation to each other, temporary seal means sealing said halves to each other along a temporary seal line beginning and ending at said fold line forming a cavity enclosing fluid between said halves and within said temporary seal line and said fold line, a fluid comprising at least one of alcohol and iodine in said cavity, and separation means for simultaneously applying separating force substantially symmetrically to both said halves of said sheet and to said temporary seal means without tearing said sheet, said separation means including means for applying simultaneously continuous separating force to open said temporary seal means along the entire length of said seal line to form a flat surface covered with the fluid while the integrity of said sheet is maintained.

2. A device as set forth in claim 1 wherein said seal line is spaced inward from the periphery of said sheet of material to provide manually engageable perimeter portions outside said seal line.

3. A device as set forth in claim 1 wherein the fluid is medicinal and at least a portion of the surface of said material enclosed by said fold line and said seal line includes textured surface means for both retaining fluid and abrading a surface to which the fluid is to be applied thereby to promote the therapeutic effect of the fluid.

4. A device as set forth in claim 3 wherein the fluid is sterile and said seal line is spaced inward from the periphery of said sheet of material to provide manually engageable perimeter portions outside said seal line.

5. The device of claim 1, said material comprising foil.

6. The device of claim 5, said material further comprising an inner plastic liner.

7. The device of claim 1, said material comprising paraffin.

8. The device of claim 1, said material comprising wax.

9. The device of claim 1, said material comprising plastic.

10. The device of claim 1, said flexible material being of oval shape when open and semi-oval shape when folded closed to enclose the fluid.

11. The device of claim 1, wherein said seal line is at least approximately parallel to a perimeter of the folded material.

12. The device of claim 1, wherein said flexible material is diamond shaped when open and triangular when folded.

13. The device of claim 1, wherein the wall surfaces of said material that are exposed to said fluid have relatively high surface energy for facilitating containment of said fluid.

14. The device of claim 1, wherein the wall surfaces of said material means that are exposed to said fluid and forms said chamber do not covalently bond with said fluid.

15. The device of claim 1, wherein said material is sealed along said seal line by applying heat to said material.

16. The device of claim 15, said material comprising foil having an inner plastic liner.

17. The device of claim 1, wherein said material is sealed along said seal line by applying pressure to said material.

* * * * *